(12) United States Patent
Mongrenier et al.

(10) Patent No.: US 9,275,262 B2
(45) Date of Patent: Mar. 1, 2016

(54) CONTAINER QUALIFICATION METHOD, ASSOCIATED STORAGE ENCLOSURE

(71) Applicant: BIOLOG, Bernay (FR)

(72) Inventors: Jean-Claude Mongrenier, Saint-German-en-Laye (FR); François Dussaux, Gretz Armainvilliers (FR)

(73) Assignee: BIOLOG (FR)

( * ) Notice: Subject to any disclaimer, the term of this patent is extended or adjusted under 35 U.S.C. 154(b) by 0 days.

(21) Appl. No.: 14/388,965

(22) PCT Filed: Mar. 27, 2013

(86) PCT No.: PCT/EP2013/056630
§ 371 (c)(1),
(2) Date: Sep. 29, 2014

(87) PCT Pub. No.: WO2013/144262
PCT Pub. Date: Oct. 3, 2013

(65) Prior Publication Data
US 2015/0015373 A1    Jan. 15, 2015

(30) Foreign Application Priority Data

Mar. 30, 2012 (FR) .................................... 12 52942

(51) Int. Cl.
*G06K 7/10* (2006.01)
*G06F 19/00* (2011.01)

(52) U.S. Cl.
CPC ........ *G06K 7/10366* (2013.01); *G06F 19/3462* (2013.01)

(58) Field of Classification Search
CPC .......... G06K 7/10366; G06K 19/0723; G06K 7/10297; G06K 19/0712; G06K 19/0717; G06K 19/07749
USPC .................................................. 340/10.1
See application file for complete search history.

(56) References Cited

U.S. PATENT DOCUMENTS

| 7,098,784 B2* | 8/2006 | Easley | G08B 25/10 340/539.1 |
| 7,911,324 B2* | 3/2011 | Breed | G01S 13/878 307/10.1 |
| 8,410,945 B2* | 4/2013 | Breed | B60J 7/0573 340/580 |
| 2003/0072676 A1 | 4/2003 | Fletcher-Haynes et al. | |

FOREIGN PATENT DOCUMENTS

| FR | 2825637 A1 | 12/2002 |
| WO | 00/45331 A1 | 8/2000 |
| WO | 2006/035465 A1 | 4/2006 |

OTHER PUBLICATIONS

International Search Report for PCT/EP2013/056630 May 14, 2013.

* cited by examiner

*Primary Examiner* — Mark Blouin
(74) *Attorney, Agent, or Firm* — Ostrolenk Faber LLP

(57) ABSTRACT

A qualification method for a container provided with an RFID tag comprising the following steps when the container is stored in a storage enclosure comprising a sensor suitable for measuring the temperature within the enclosure and an RFID reader:

a/ radiofrequency transmission by reader of a message comprising a value representative of a temperature measurement in the enclosure; step a/ being reiterated after each measurement moment of a plurality of predetermined successive measurement moments;

b/ storage, by the RFID tag of the container, of the value included in said message received, the memory of the RFID tag comprising successively stored temperature values each associated with a distinct determined measurement moment;

c/ qualification or disqualification of the container as a function of a comparison between the number of temperature values stored for the container and the number of said determined measurement moments.

15 Claims, 2 Drawing Sheets

CONTAINER QUALIFICATION METHOD, ASSOCIATED STORAGE ENCLOSURE

This application is a National Stage application of PCT international application PCT/EP2013/056630, filed on Mar. 27, 2013 which claims the priority of French Patent Application No. 1252942 entitled "CONTAINER QUALIFICATION METHOD, ASSOCIATED STORAGE ENCLOSURE", filed with the French Patent Office on Mar. 30, 2012, both of which are incorporated herein by reference in their entirety.

The present invention relates to a qualification method for a container provided with first wireless telecommunications means comprising a memory.

Such containers are for example pouches containing biological products such as blood products (pouches of primary blood, plasma, platelets, red blood cells, etc.) or cellular engineering products (stem cells, etc.), or drug pouches such as chemotherapy pouches.

It is crucial to be able to track the pouches, and to associate a certain amount of information with them (information and key dates relative to the contents, etc.).

It is in particular important to keep track of the information making it possible to qualify or disqualify the pouches based on the age of the pouch and the atmospheric conditions for storage, including temperature, pressure and humidity. In fact, the aging of the pouches varies depending on the storage conditions.

Document EP 1,397,104 describes a technique according to which a blood pouch is stored in a controlled atmosphere enclosure; a computation of an updated aging index is done regularly based on an average temperature in the enclosure and the time that has elapsed since the last update. The updated aging index is next recorded in the RFID tag of the blood pouches, with the date and time of the update. It is also mandatory for an updated aging index to be recorded in the RFID tag of that pouch, each time the pouch is placed in/removed from a controlled atmosphere enclosure.

There is, however, a need for a technique making it possible to detect breaks in the storage process for the pouches in order, if necessary, to disqualify pouches for which the continuity of the atmospheric storage conditions is not guaranteed.

To that end, according to the invention, a method of the aforementioned type is characterized in that it comprises the following steps when the container is stored in a container storage enclosure, said enclosure comprising at least one atmospheric sensor suitable for measuring, within the enclosure, at least one atmospheric parameter from among the temperature, pressure and humidity, and at least second wireless telecommunications means:

a/ radiofrequency transmission by the second wireless telecommunications means from the enclosure, to first wireless telecommunications means of the container, of a message comprising a value representative of a result of a measurement of said parameter in the enclosure; step a/ being reiterated after each measurement moment of a plurality of predetermined successive measurement moments;

b/ for each of said messages received by the first wireless telecommunications means of the container, storage, by said first wireless telecommunications means of the container, of the representative value comprised in the received message, the memory of the first wireless telecommunications means of the container including values representative of the results of measurements of said parameter successively stored and each associated with a distinct predetermined measurement moment;

according to which the method further comprises a step for qualifying or disqualifying the container as a function of at least one comparison between the number of values representative of a result of a measurement of said parameter that are stored in the memory of the first wireless telecommunications means of the container and the number of said predetermined measurement moments.

Such a method makes it possible to increase the guarantee of the continuous presence of a container in the enclosure of the container and to detect discontinuities both in the presence of the container in the enclosure and in the temperature measurements.

In embodiments, the method according to the invention further includes one or more of the following features:

the first wireless telecommunications means of the container include an RFID tag and the second wireless telecommunications means of the enclosure include an RFID reader;

in step a/, the message further comprises an indication of the moment of said predetermined measurement and in step b/, said indication is stored matching said representative value;

steps a/ and b/ are reiterated for each period of length T;

T is comprised between 10 seconds and 6 hours;

the container is qualified or disqualified based on a number of returned measurement moments for which the memory of the first wireless telecommunications means of the container does not include a value representative of the measurement result, said measurement moments being situated between the two measurement moments for which representative values of a result have been stored in the memory of the first telecommunications means;

a container is further qualified or disqualified based on representative values stored in the memory of the first wireless telecommunications means of the container;

the method comprises the following steps when the container is stored in a container transport enclosure, then transported between a departure point and a destination point in said transport enclosure, said transport enclosure comprising a sensor suitable for measuring the value of at least one atmospheric parameter from among the temperature, pressure and humidity within the enclosure and three wireless telecommunications means comprising a memory:

recording, during transport, a value representative of a result of a measurement of said parameters for each of several successive predetermined measurement moments, in the memory of the third wireless telecommunications means of the transport enclosure;

transmission, by the third wireless telecommunications means of the transport enclosure, said representative values to a processing device comprising fourth wireless telecommunications means and situated at the destination point;

qualification or disqualification of the container based on said representative values received by the processing device;

third wireless telecommunications means comprise an RFID tag and the fourth wireless telecommunications means comprise an RFID reader; and the method further comprises the following steps:

transmission, from the fourth wireless telecommunications means of the processing device to the first wireless communication means of the container, of at least said representative values received by the processing device;

reception of said representative values by the first wireless communication means of the container and storage by said first communication means of said parameter values received in the memory.

According to a second aspect, the present invention proposes a storage enclosure for containers comprising at least one atmospheric condition sensor suitable for measuring, within the enclosure, at least one atmospheric parameter from among the temperature, pressure and humidity, and said enclosure comprising second wireless telecommunications means suitable for communicating with first wireless telecommunications means of at least one container stored in the enclosure, said storage enclosure being characterized in that it is suitable for transmitting, after each measurement moment of a plurality of predetermined successive measurement moments, to first wireless telecommunications means of said container, a message comprising a value representative of a result of a measurement of said parameter in the enclosure for the storage, by the first wireless telecommunications means, of the representative value, and in that it is suitable for qualifying or disqualifying a container as a function of at least one comparison between the number of representative values of a result of the measurement of said parameter that are stored in the memory of the first wireless telecommunications means of the container and the number of said predetermined measurement moments.

These features and advantages of the invention will appear upon reading the following description, provided solely as an example, and done in reference to the appended drawings, in which.

Figure 3:
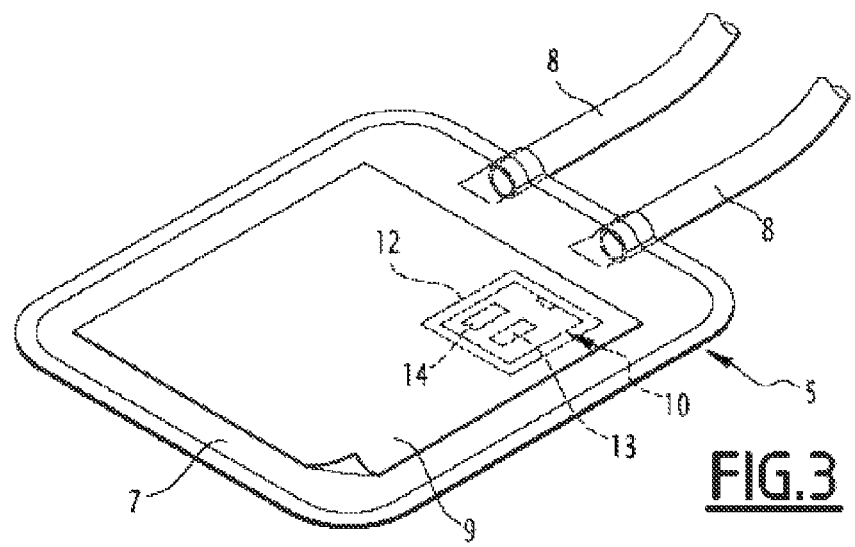
FIG. 3 shows a blood pouch considered in one embodiment of the invention.

In FIG. 3, a pouch 5 is shown, intended to contain blood in this case.

In a known manner, that pouch 5 is a tight blood container made from a breathable plastic material allowing metabolism, of the PVC (polyvinyl chloride), polycarbonate or PEG (polyethylene glycol) type.

The pouch 5 includes tubings 8 that are sealed, for example by welding. These tubings 8 were used, before sealing, to insert the blood into the pouch 5.

An adhesive tag 9 is adhered on an outer face of the pouch 5. This adhesive tag 9 includes an RFID chip 10.

The RFID chip 10 includes a radiofrequency antenna 12, a memory 13 and optionally a microprocessor 14.

Figure 1:
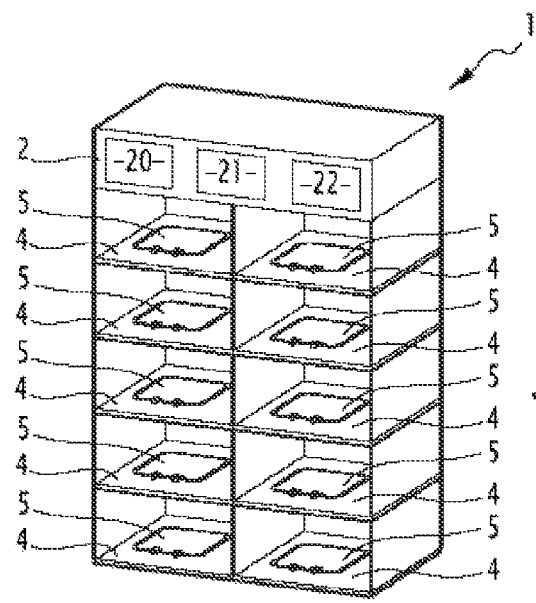
FIG. 1 shows a container storage enclosure in one embodiment of the invention.

FIG. 1 shows a storage enclosure 1 with a controlled atmosphere designed to store blood pouches similar to the blood pouch 5 shown in FIG. 3.

The enclosure 1 includes a control stage 2, including a microcontroller 21, a memory 22 and a thermometer 20.

The thermometer 20 is suitable for measuring the current temperature within the enclosure 1.

The enclosure 1 also includes means, not shown, designed for ventilation and to regulate the temperature based on the currently measured temperature, so as to keep the temperature within the enclosure 1 within a given range, for example [2° C., 6° C.], where ° C. represents the Celsius unit.

The enclosure 1 further comprises slots 4 designed for blood pouch storage 5. In the case in question, one blood pouch is stored per slot. In other embodiments, several pouches are stored in one slot 4.

Figure 2:
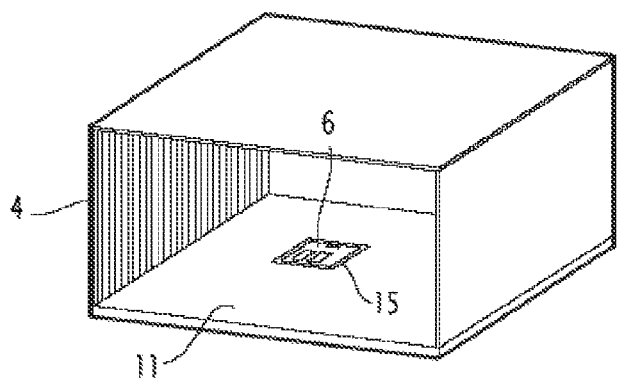
FIG. 2 shows a storage slot for the enclosure of FIG. 1.

FIG. 2 shows a slot 4 in more detail.

A slot 4 includes a horizontal support 11 on which a pouch 5 to be stored is placed. The support 11 includes an RFID reader 6 provided with an antenna 15 and suitable for communicating by radiofrequency with a blood pouch 5 positioned in the slot 4 (the pouch 5 preferably being positioned such that its face including the RFID tag 10 is in contact with the RFID reader 6 of the slot 4).

A program P1 stored in the memory 22 of the enclosure 1 comprises software instructions suitable for carrying out the following steps that are carried out by the enclosure when the program P1 is run by the microcontroller 21 of the enclosure 1.

The following steps are carried out for every period of length T1 by the control stage 2 of the enclosure 1 (see FIG. 4):

reading the temperature indicated by the thermometer 20 and storing the read temperature with the date and time of the reading in the memory 22 of the enclosure 1 (step 100);

controlling the RFID reader of each slot 4 (optionally only the RFID reader of each occupied slot when the control stage stores a list of occupied slots) to carry out the following step 101;

transmission by the RFID reader 6 of each of the slots 4, via its antenna 15, to the pouch 5, of a message including the read temperature, as well as the date and time of the reading (step 101), and commanding the recording in the memory 13 of the RFID chip 10 of the pouch of those associated temperature, date and time values.

(It will be recalled that in a known manner, the RFID reader transmits energy through its antenna intended to activate and power a nearby RFID chip or RFID "tag", and to make it possible to write data in the memory of the RFID chip, or for the RFID chip to send information.)

Figure 4:
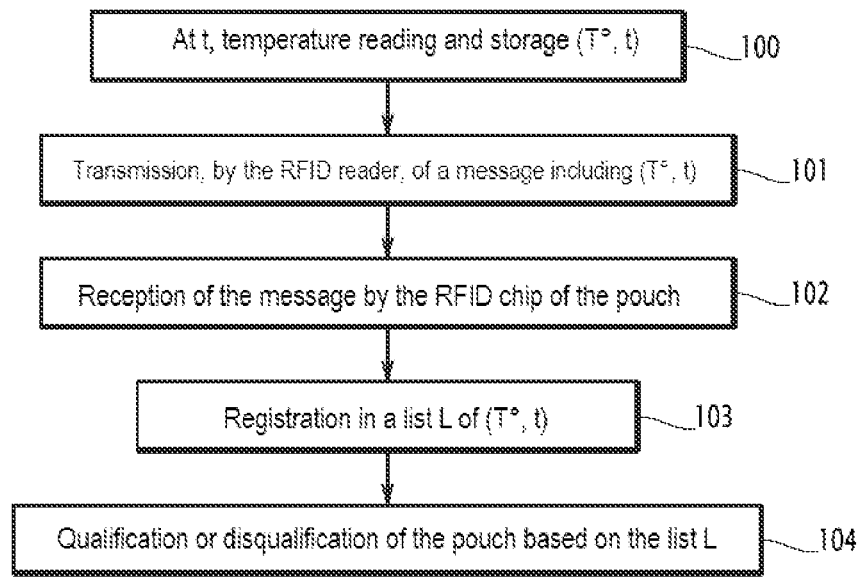
FIG. 4 is a flowchart of a method in one embodiment of the invention.

The following steps are next carried out by a pouch 5 located in one of those slots, as shown in FIG. 4:

reception, by the RFID chip 10 of the pouch 5 via its antenna 12, of the message transmitted by the RFID reader 6 of the slot 4 in which the pouch 5 is located (step 102);

recording, in a data list L stored in the memory 13 of the pouch 5, a set including the read temperature, the date and time of the temperature reading (step 103), following sets previously stored if applicable, including a temperature read with the date and time of the reading.

In one embodiment, T1 is comprised in the following value range [30 s, 60 s], "s" indicating the "second" unit.

In another embodiment, T1 is comprised in the following value range [30 s, 10 min], "min" indicating the "minute" unit.

In another embodiment, T1 is comprised in the following value range [30 s, 6 h], "h" indicating the "hour" unit.

The value of T1 is chosen based on the effect of the temperature variations on the product contained in the pouch and atmospheric storage constraints. For example, in the case at hand where the pouches contain blood, T1 is chosen to be equal to 10 min.

Thus, a blood pouch 5 stored between a moment Td and a moment Tf will nominally include, in the data list L stored in its RFID chip 10, the n+1 following sets ($Temp_{Td+dt+iT1}$ being the temperature read at moment Td+d+iT1):

(Td+dt+iT1, $Temp_{Td+dt+iT1}$) with i being an equal integer varying from 0 to n, with dt≤T1 and 0≤Tf−(Td+dt+nT1)≤T1.

Thus, by analyzing the data list L stored in the RFID chip 10 of the pouch 5 having stayed in the enclosure 1 between the known moments Td and Tf, a discontinuity regarding that storage of the pouch 5 in the enclosure 1 is detectable when the list does not include the sets nominally present as indicated above.

Thus, the absence of one or more data set(s) (Td+dt+iT1, $Temp_{Td+dt+iT1}$) can reveal a discontinuity in the storage: for example, the pouch 5 was outside the enclosure 1 at a time when it should have received that or those data set(s). It is also possible that a failure may have occurred in the supply of electricity to the enclosure when the enclosure should have used its RFID readers to send that or those data set(s).

It is therefore possible, if a data set or k consecutive data sets $(Td+dt+iT1, Temp_{Td+dt+iT1}), \ldots, (Td+dt+(i+k-1)T1, Temp_{Td+dt+(i+k-1)T1})$ are missing, in particular with $0<i<n$ and $0 \leq k < n-i+1$, to determine the corresponding maximum duration during which it is not possible to guarantee the presence of the pouch in the enclosure, which is $(k-i+2)T1$.

Then, depending on the maximum duration during which the presence of the pouch 5 in the enclosure 1 under the required storage constraints is not guaranteed, and further optionally based on the temperature $Temp_{Td+dt+(i-1)T1}$ read at the moment preceding the absence of data and/or the temperature $Temp_{Td+dt+(i+k)T1}$ read at the moment following the absence of data, the pouch 5 is qualified or disqualified regarding its use for a future transfusion, for example, in a step 104.

Furthermore, the qualification/disqualification of the pouch 5 is also done based on temperature values recorded in the RFID chip 10 of the pouch 5, optionally averaged over the presence time in the enclosure 1.

This qualification or disqualification operation may be carried out by a computer device coupled with an RFID reader outside the enclosure 1, querying the RFID chip 10 of the pouch 5 once removed from the enclosure 1.

In one embodiment, this qualification or disqualification operation is performed by the control stage 2 of the enclosure 1 using the RFID reader 6 of the slot 4 for storing the pouch 5, for example at regular moments and/or when the pouch 5 is taken out of the enclosure 1, that removal being detected by the enclosure 1 itself or indicated to the enclosure 1 by an operator interacting with the control stage 2 of the enclosure 1.

In another embodiment, the result of the qualification/disqualification operation is stored in the RFID chip 10 of the pouch 5 using the RFID reader used to perform that operation.

In one embodiment of the invention, the message sent by the RFID reader 6 in step 101 includes, in place of the date and time of the temperature reading, an identifier of the time and date of the reading, for example a position in the memory 22 of the enclosure 1 corresponding to the date and time of the temperature reading.

In one embodiment of the invention, the message sent by the RFID reader 6 in step 101 includes an indicator in place of the read temperature. The value of that indicator is determined by the control stage 2 based on the temperature currently measured, and may for example assume two distinct values (values 0 and 1, or OK and KO). The current value is for example 0, or KO, when the temperature currently measured is not in the given range, that range for example being [+2° C., +6° C.]. The current value is for example 1 or OK when the temperature is in the given range.

In one embodiment, the message does not include a temperature reading date/time, or a date/time identifier. In such a case, the qualification/disqualification is done based on verification of the number of values actually stored in the RFID chip 10 of the pouch 5, of the temperature or indicators relative to the temperature values compared to the number of values that should theoretically have been stored based on the frequency of the recording commands, whether regular or not, in step 101 during the storage period of the pouch in the enclosure.

In another embodiment of the invention that may or may not be implemented in the embodiments described above, a transport enclosure is considered comprising a sensor suitable for measuring the value of at least one atmospheric parameter within the enclosure, for example temperature, and an RFID tag comprising a memory.

This transport enclosure is suitable for recording, in the memory of the RFID tag of the transport enclosure, parameter values successively measured during the transport, associated with time indicators representing the successive time measurements.

In one embodiment, a pouch 5 that may or may not have stayed in the enclosure 1 is transported from a starting location to a destination location within such a transport enclosure, for example a transport box 30, with or without a regulated atmosphere.

The transport box is suitable for containing one or more pouches 5.

Figure 5:
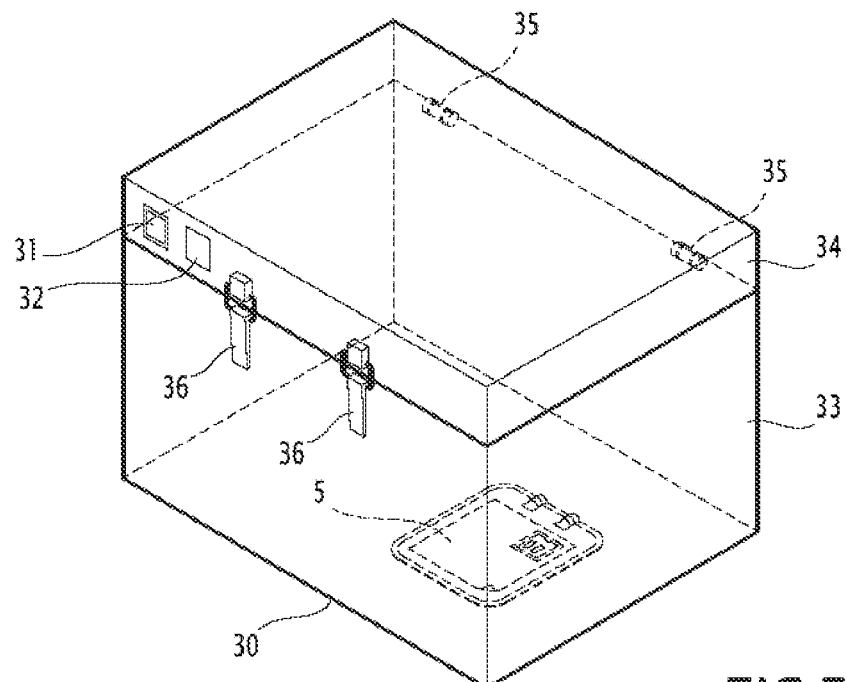
FIG. 5 shows a transport box.

The transport box 30, as shown in FIG. 5, includes a case 33 covered with a lid 34. The case 33 and the lid 34 are for example connected by a hinge 35 allowing the lid to be opened and closed by rotating the lid. Furthermore, fastening elements 36 make it possible to lock the lid once it is closed on the case, in particular during the transport operations, so as to limit the temperature variations of the pouches contained in the box.

The transport box 30 further includes an RFID recorder 31 comprising a microprocessor, a memory, and a radiofrequency antenna.

The transport box 30 further includes a thermometer 32 suitable for measuring the temperature in the part of the box containing the pouch 5 and optionally other pouches.

The transport box 30 is suitable for performing, during each period of length T2 (for example T2=T1), a reading of the temperature indicated by the thermometer 32 of the box and successively storing each read temperature with the date and time of the corresponding reading in the memory of the RFID recorder 31 along the conveyance between the starting location and the arrival location.

When the transport box 30 is presented to an operator at the destination point, that operator uses an RFID reader coupled with a computer qualification device to read the temperatures respectively associated with the reading of the corresponding dates and times that have been successively stored in the RFID recorder 31 of the transport box.

The computer qualification device is suitable for implementing a qualification/disqualification operation of the pouch 5 and, if applicable, of the other pouches transported in the box, the qualification operation being similar to that described above in step 104, but this time as a function of temperatures, dates and times of readings extracted from the transport box 30.

Thus, the pouches thus delivered may be refused or accepted without needing to open the transport box.

In one embodiment, the result of the qualification/disqualification operation is recorded in the RFID chip 10 of the pouch 5 by the RFID reader coupled with the computer device, as well as the time and date of the operation, with an identifier of the computer device.

In one embodiment, when the pouch 5 is qualified, the temperatures or indicators associated with the temperature reading times read by the computer device are also recorded in the RFID chip 10 of the pouch 5 by the RFID reader coupled to the computer device.

As in the case of the aforementioned enclosure 1, such arrangements make it possible to test the quasi-continuous presence (depending on the value of T1 or T2) of the pouches within the enclosure, by associating those presence tests with the temperature then prevailing in the enclosure or box.

In one embodiment, the RFID communications implemented between an RFID reader and an RFID chip indicated in the embodiments described above are encrypted.

Embodiments of the invention have been described above considering the temperature parameter. Any other parameter illustrating the atmospheric storage conditions may be considered to implement the invention in place of the temperature, or in addition.

Embodiments of the invention have been described above considering blood pouches. The invention may of course be implemented for any type of pouch designed to contain products whose use is subject to strict storage constraints. In one embodiment, the invention applies to pouches containing biological products such as blood products (pouches of primary blood, plasma, platelets, red blood cells, etc.) or cellular engineering products (human or animal cells, in particular human or animal stem cells, products from human or animal cells). In another embodiment, the invention applies to drug pouches or therapeutic preparation pouches containing one or more active ingredients or medicaments, such as chemotherapy pouches (generally containing a solute and one or more chemotherapy active ingredients). More generally, the invention applies to any product designed to be infused in a patient (human or animal).

The pouch storage enclosure 1 considered in reference to FIGS. 1 and 2 includes storage slots in which the pouches are positioned horizontally. The invention may of course be implemented with any other storage configurations.

Furthermore, in the described example, an RFID reader was specific to each slot: the invention may be implemented in cases where a same RFID reader is used for several slots.

The invention claimed is:

1. A qualification method for a container provided with first wireless telecommunications means comprising a memory, said method comprising the following steps when the container is stored in a container storage enclosure, said enclosure comprising at least one atmospheric sensor suitable for measuring, within the enclosure, at least one atmospheric parameter from among the temperature, pressure and humidity, and at least second wireless telecommunications means:
   a/ radiofrequency transmission by the second wireless telecommunications means of the enclosure, to first wireless telecommunications means of the container, of a message including a value representative of a result of a measurement of said parameter in the enclosure; step a/ being reiterated after each measurement moment of a plurality of determined successive measurement moments;
   b/ for each of said messages received by the first wireless telecommunications means of the container, storage, by said first wireless telecommunications means of the container, of the representative value included in the received message, the memory of the first wireless telecommunications means of the container including values representative of the results of measurements of said parameter successively stored and each associated with a distinct determined measurement moment;
   according to which the method further comprises a step for qualifying or disqualifying the container as a function of at least one comparison between the number of values representative of a result of a measurement of said parameter that are stored in the memory of the first wireless telecommunications means of the container and the number of said determined measurement moments.

2. The method according to claim 1, wherein the first wireless telecommunications means of the container include an RFID tag and the second wireless telecommunications means of the enclosure include an RFID reader.

3. The method according to claim 1, wherein in step a/, the message further comprises an indication of the moment of said determined measurement and in step b/, said indication is stored matching said representative value.

4. The method according to claim 1, wherein steps a/ and b/ are reiterated for each period of length T.

5. The method according to claim 4, wherein T is comprised between 10 seconds and 6 hours.

6. The method according to claim 1, wherein the container is qualified or disqualified as a function of a number of determined measurement moments for which the memory of the first wireless telecommunications means of the container does not include a value representative of a measurement result, said measurement moments being situated between the two measurement moments for which representative values of a result have been stored in the memory of the first telecommunications means.

7. The method according to claim 1, wherein a container is further qualified or disqualified based on the representative values stored in the memory of the first wireless telecommunications means of the container.

8. The method according to claim 1, comprising the following steps when the container is stored in a container transport enclosure, then transported between a departure point and a destination point in said transport enclosure, said transport enclosure comprising a sensor suitable for measuring the value of at least one atmospheric parameter from among the temperature, pressure and humidity within the enclosure and three wireless telecommunications means comprising a memory:
   recording, during transport, a value representative of a result of a measurement of said parameters for each of several successive determined measurement moments, in the memory of the third wireless telecommunications means of the transport enclosure;
   transmission, by the third wireless telecommunications means of the transport enclosure, said representative values to a processing device comprising fourth wireless telecommunications means and situated at the destination point;
   qualification or disqualification of the container based on said representative values received by the processing device.

9. The method according to claim 8, wherein third wireless telecommunications means comprise an RFID tag and the fourth wireless telecommunications means comprise an RFID reader.

10. The method according to claim 8, further comprising the following steps:
    transmission, from the fourth wireless telecommunications means of the processing device to the first wireless communication means of the container, of at least said representative values received by the processing device;
    reception of said representative values by the first wireless communication means of the container and storage by said first communication means of said parameter values received in the memory.

11. A storage enclosure for containers comprising at least one atmospheric condition sensor adapted for measuring, within the enclosure, at least one atmospheric parameter from among the temperature, pressure and humidity, and said enclosure comprising second wireless telecommunications means adapted for communicating with first wireless telecommunications means of at least one container stored in the enclosure, said storage enclosure being adapted for transmitting, after each measurement moment of a plurality of determined successive measurement moments, to first wireless telecommunications means of said container, a message including a value representative of a result of a measurement of said parameter in the enclosure for the storage, by the first wireless telecommunications means, of the representative value;

and being adapted for qualifying or disqualifying a container as a function of at least one comparison between the number of representative values of a result of the measurement of said parameter that are stored in the memory of the first wireless telecommunications means (10) of the container and the number of said determined measurement moments.

12. The enclosure according to claim 11, wherein the second wireless telecommunications means of the enclosure include an RFID reader, and the first wireless telecommunications means of the container include an RFID tag.

13. The enclosure according to claim 11, suitable for inserting an indication of the time of said determined measurement into the message.

14. The enclosure according to claim 11, wherein the measurement moments are separated by a period of length T.

15. The enclosure according to claim 14, wherein T is comprised between 10 seconds and 6 hours.

* * * * *